United States Patent [19]

Ferrante et al.

[11] Patent Number: 5,098,436
[45] Date of Patent: Mar. 24, 1992

[54] MODULAR GUIDE FOR SHAPING OF FEMUR TO ACCOMMODATE INTERCONDYLAR STABILIZING HOUSING AND PATELLAR TRACK OF IMPLANT

[75] Inventors: Joseph M. Ferrante, Cordova, Tenn.; Leo A. Whiteside, Chesterfield, Mo.; Bradley J. Coates, Cordova, Tenn.

[73] Assignee: Dow Corning Wright Corporation, Arlington, Tenn.

[21] Appl. No.: 666,153

[22] Filed: Mar. 7, 1991

[51] Int. Cl.5 .......................... A61B 17/56; A61F 2/38
[52] U.S. Cl. ...................... 606/88; 606/87; 606/96; 606/53; 623/20; 623/16
[58] Field of Search .................... 606/86–88, 606/89, 96, 99, 53, 100; 623/20, 16

[56] References Cited

U.S. PATENT DOCUMENTS

| | | | |
|---|---|---|---|
| 4,474,177 | 10/1984 | Whiteside | 606/80 |
| 4,721,104 | 1/1988 | Kaufman et al. | 606/88 |
| 4,736,737 | 4/1988 | Fargie et al. | 606/88 |
| 4,926,847 | 5/1990 | Luckman | 606/88 |
| 5,035,699 | 7/1991 | Coates | 606/87 X |

*Primary Examiner*—Randall L. Green
*Assistant Examiner*—D. Willse
*Attorney, Agent, or Firm*—John L. Chiatalas

[57] ABSTRACT

Modular surgical instrumentation and a method of using same is provided, according to the invention. The instrumentation comprises a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove in a portion of the selected area exposed through the opening. A second bracket defines a linear slotted bore extending generally parallel to the long axis of the femur for guiding a second shaping tool to form a relatively deep recess accommodating an intercondylar stabilizing housing of a knee implant. The second bracket has an internal surface defining a shape adapted for releasable engagement with the curved track, including mechanism for accurately aligning the slotted bore relative to the opening while forming the recess. The method of the invention comprises the steps of seating the first bracket described above on the distal aspect of the resected femur and moving the first shaping tool along the curved track to form a patellar groove in a selected area thereof. The first shaping tool is then withdrawn and, leaving the first bracket in place, the second bracket described above is seated on the curved track so that the slotted bore of the second bracket is accurately aligned with the opening of the first bracket, after which a second shaping tool is introduced through the bore to form a recess accommodating the intercondylar-stabilizing housing of the implant.

11 Claims, 5 Drawing Sheets

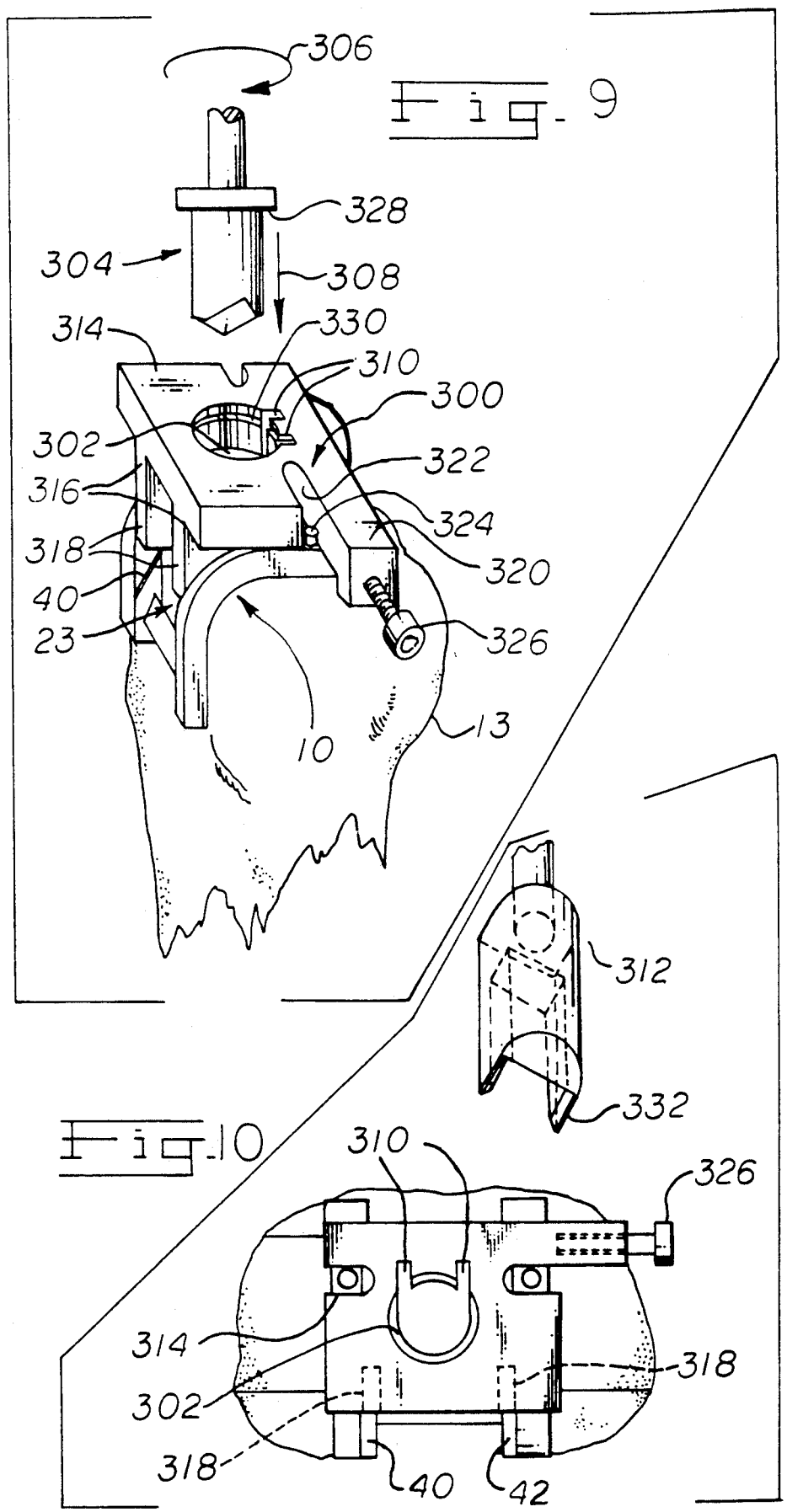

MODULAR GUIDE FOR SHAPING OF FEMUR TO ACCOMMODATE INTERCONDYLAR STABILIZING HOUSING AND PATELLAR TRACK OF IMPLANT

TECHNICAL FIELD

This invention generally relates to surgical devices for use by orthopedic surgeons in the implantation of distal femoral knee prostheses, particularly in cases where a patellar prosthesis is also implanted and, more particularly, where an intercondylar stabilizing housing is provided in the implant.

BACKGROUND

Surgical instruments for various bone shaping or resection operations, required in the implantation of prosthetic devices, have been devised to assist orthopedic surgeons in accurately performing the necessary cutting steps.

One example of such instrumentation is U.S. Pat. No. 4,474,177 to Whiteside, disclosing a device and method which utilize an intermedullary rod for aligning a shaping tool(s) to make several angular resection cuts using a common reference axis precisely established by the rod.

Another example is the apparatus described U.S. Pat. No. 4,721,104 to Kaufman and Whiteside, which describes a femoral shaping apparatus employing a template having a straight slot therein for cutting a relatively deep recess for an intercondylar stabilizing housing of a knee implant. The patent, however, does not disclose a cutting guide having a curved track useful for forming a groove to accommodate a patellar track on such a prosthesis.

Heretofore it has been common practice for a surgeon to form a patellar track groove in a resected distal femur, if required, due to the nature of the particular knee prosthesis being implanted, by use of various cutting or abrading tools or instruments without aid of any type of locating or guiding instrument. In design and seating of a prosthesis it is important to retain the original patella/femoral joint line to avoid placing undue stress on the patella and its connective tissues.

U.S. Pat. application Ser. No. 462,268, filed Jan. 9, 1990 in the name of Coates, et. al, describes an improved system for accurate placement and cutting of a groove to accommodate a patellar track portion of a prosthesis to insure accurate seating of the prosthesis for long term wear and stability of a patellar prosthesis.

There still remains a need for using common surgical instrumentation to form both a groove and deep recess in the resected distal femur, respectively accommodating a patellar track and intercondylar stabilizing housing of the implant.

SUMMARY OF INVENTION AND ADVANTAGES

Modular surgical instrumentation and a method of using same is provided, according to the invention. The instrumentation comprises a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove in a portion of the selected area exposed through the opening. A second bracket defines a linear slotted bore extending generally parallel to the long axis of the femur for guiding a second shaping tool to form a relatively deep recess accommodating an intercondylar stabilizing housing of a knee implant. The second bracket has an internal surface defining a shape adapted for releasable engagement with the curved track, including means for accurately aligning the slotted bore relative to the opening while forming the recess.

The method of the invention comprises the steps of seating the first bracket described above on the distal aspect of the resected femur and moving the first shaping tool along the curved track to form a patellar groove in a selected area thereof. The first shaping tool is then withdrawn and, leaving the first bracket in place, the second bracket described above is seated on the curved track so that the slotted bore of the second bracket is accurately aligned with the opening of the first bracket, after which a second shaping tool is introduced through the bore to form a recess accommodating the intercondylar-stabilizing housing of the implant.

An advantage of the invention is that a patellar groove may be formed in the femur utilizing a cutting guide which need not be removed in order to form a recess for an intercondylar-stabilizing housing using a second cutting guide, the two guides being cooperable with one another in a modular structure.

Another advantage of the invention is that alignment of the recess with the patellar groove is based on the same cutting guide and, hence, is more accurate than the use of subsequent and separate guides.

BRIEF DESCRIPTION OF THE DRAWINGS

The invention will be further explained with reference to the following Detailed Description and Drawings wherein:

FIG. 9 is a perspective view of a shaping guide used with the U-shaped bracket of the invention, to form a recess for accommodating the intercondylar stabilizing housing of an implant; and FIG. 10 is a top view of FIG. 9 showing another tool for performing a further shaping operation.

DETAILED DESCRIPTION OF ONE OR MORE PREFERRED EMBODIMENTS

Figure 1:
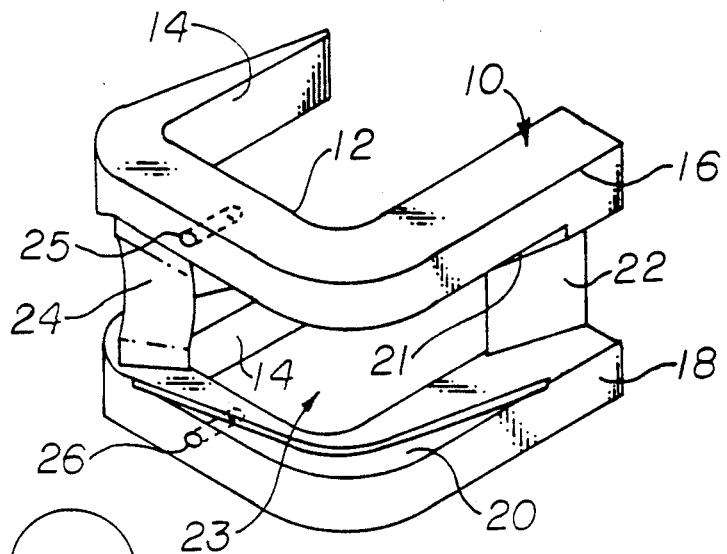
FIG. 1 is a perspective view of a U-shaped cutting guide of this invention adapted to fit over the distal end of a resected femur.
Figure 2:
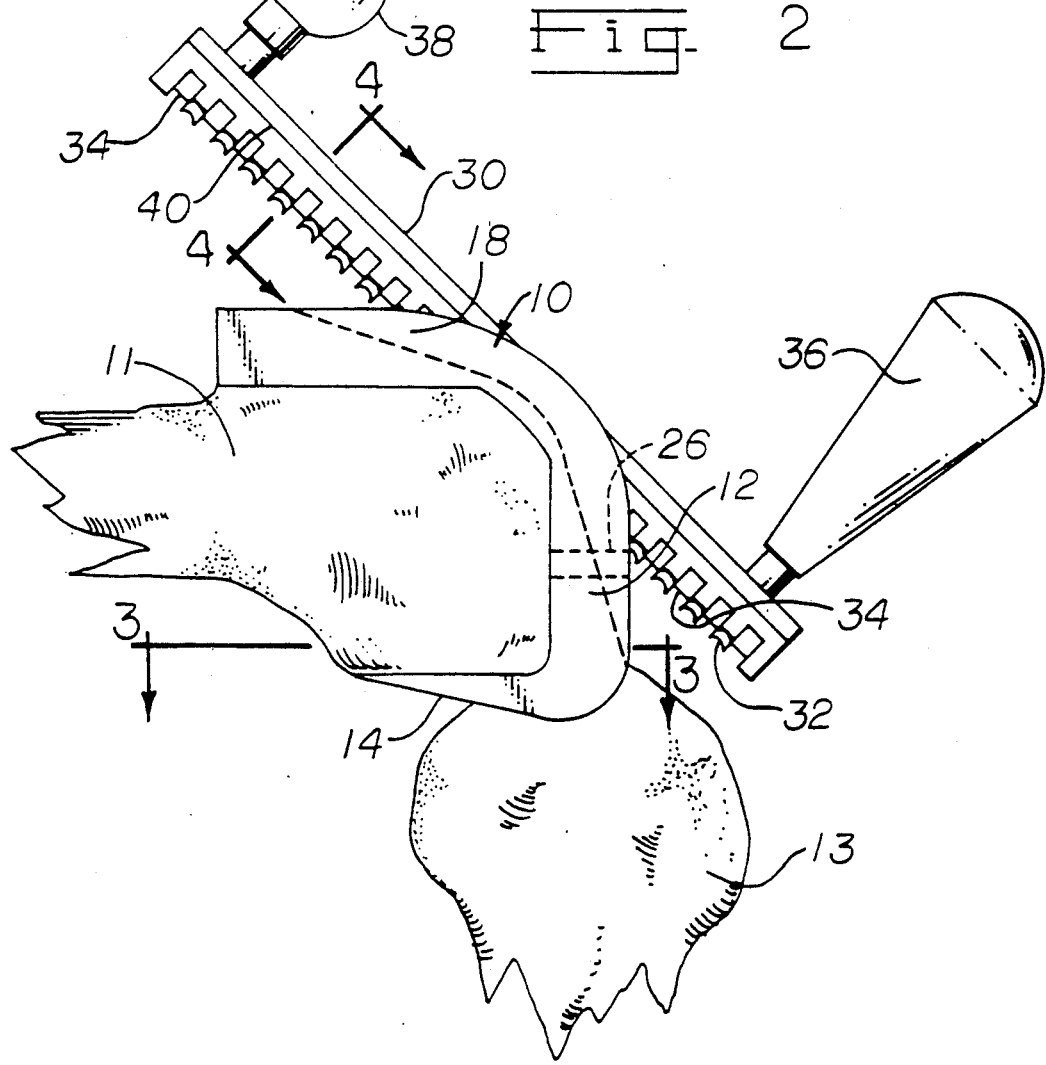
FIG. 2 is a side view illustrating the use of the U-shaped guide of this invention in place on a femur in conjunction with a cutting tool.
Figure 3:
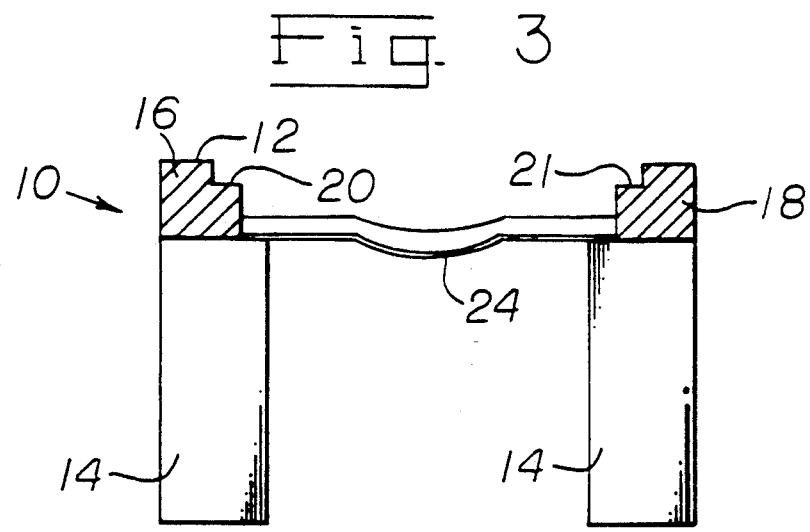
FIG. 3 is a cross-sectional view of the U-shaped cutting guide of FIG. 1, taken along line 3—3 of FIG. 2.

Referring more particularly to the Drawings, there is seen in FIG. 1 a cutting guide element 10 of generally U-shaped configuration having a section 12 adapted to fit over the distal end of a resected femur 11 as shown in FIG. 2. End 14 is adapted to fit on the posterior side of the resected femur and consists of 2 arms adapted to fit over the medial and lateral condyles of the femur. The anterior side of the cutting guide device consists of ends 16 and 18 which are a continuation of the distal surface contacting portion 12 and are adapted to closely fit over the anterior side of the resected femur as indicated in FIG. 2. Channels 20 and 21 are cut or sunk into the central edges of portion 16 and 18 of the device to form a curved track in which the cutting device can be moved during the course of cutting procedures.

The central portion of the cutting guide 10 consists of an elongated opening 23 which exposes at least the distal and anterior aspects of the resected femur so that a patellar groove may be cut therein. Connecting members 22 and 24 serve to connect the device together into an integral structure. The distal surfaces of the connecting members may also be curved as illustrated with element 24 to provide room for the cutting tool during use.

Holes 25 and 26 are preferably formed in the distal surface portion of the guide member in order to provide a means for securing the guide to the resected femur. These holes can be used to accurately drill holes into the femur for the purpose of installing anchoring pins to fix the guide to the femur. These holes are preferably positioned so that they will receive anchoring pegs on the actual implant.

Figure 4:
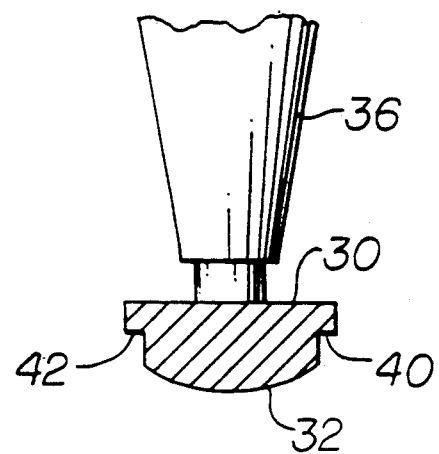
FIG. 4 is a cross-sectional view of the cutting tool shown in FIG. 2, taken along line 4—4.

As best seen in FIG. 2 a hand-operated cutting tool 30 may be employed in conjunction with cutting guide 10. Tool 30 is provided with a generally convex-shaped cutting portion 32, the cross-section of which is seen in FIG. 4. A series of cutting teeth 34 are positioned along the length of cutting surface 32. The edges of surface 32 are provided with ledges 40 and 42 along the entire length thereof. Ledges 40 and 42 act as track-engaging means so that the cutting tool 10 can be moved along a desired central course to cause resection of a patellar channel in the distal and anterior surfaces of femur 11. With the embodiment of FIG. 2, the surgeon can by hand reciprocate cutting tool 30 in guide 10 using handles 36 and 38.

Figure 5:
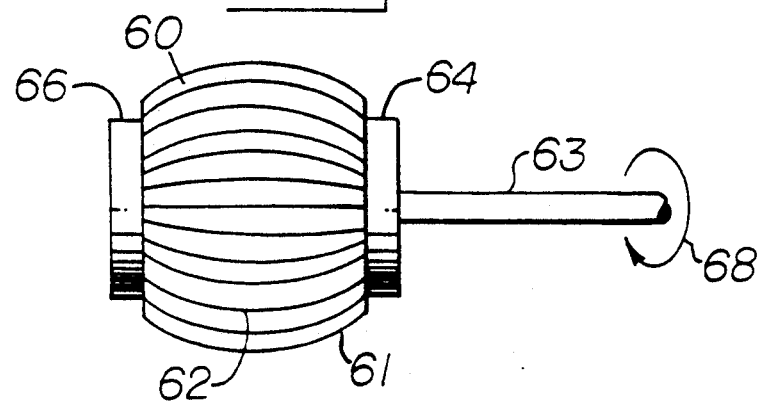
FIG. 5 is a side view of an alternative cutting tool for use with the U-shaped guide, which may be power driven.

In the embodiment of FIG. 5, an alternative cutting tool 60 is employed which is provided with an annular convex-shaped cutting surface 61. Surface 61 is provided with a series of cutting teeth 62 around the circumference thereof for purposes of resection of femur 11. Shoulders 64 and 66 are provided on opposite ends of the cutting surface so that the cutting tool 60 can be moved along cutting guide tracks 20 and 21. Shaft 63 is provided so that tool 60 can be driven by a conventional rotary power tool (not shown) so that it rotates as indicated by arrow 68.

Figure 6:
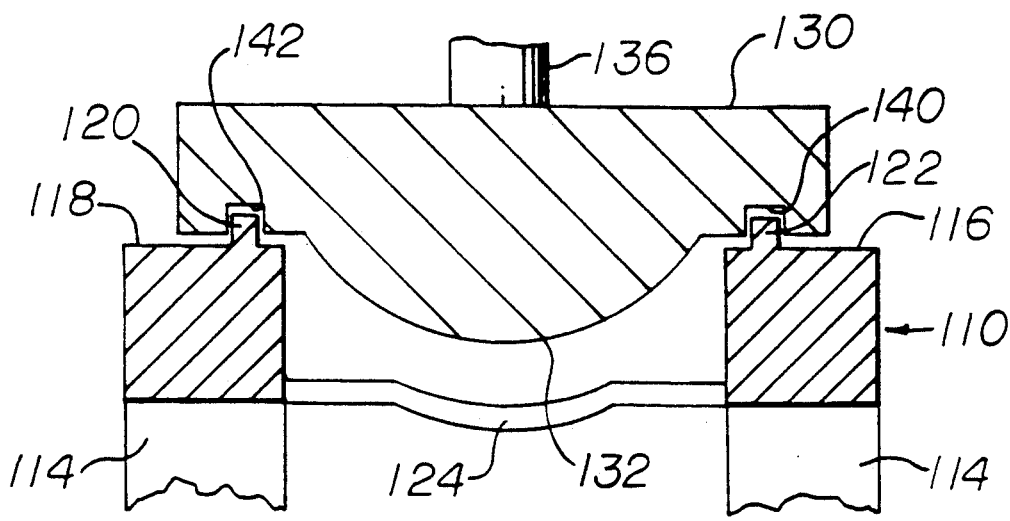
FIG. 6 is a cross-sectional view of a further embodiment of the U-shaped guide in conjunction with a cutting tool of the invention, taken along a cross-section similar to that of FIG. 3.
Figure 7:
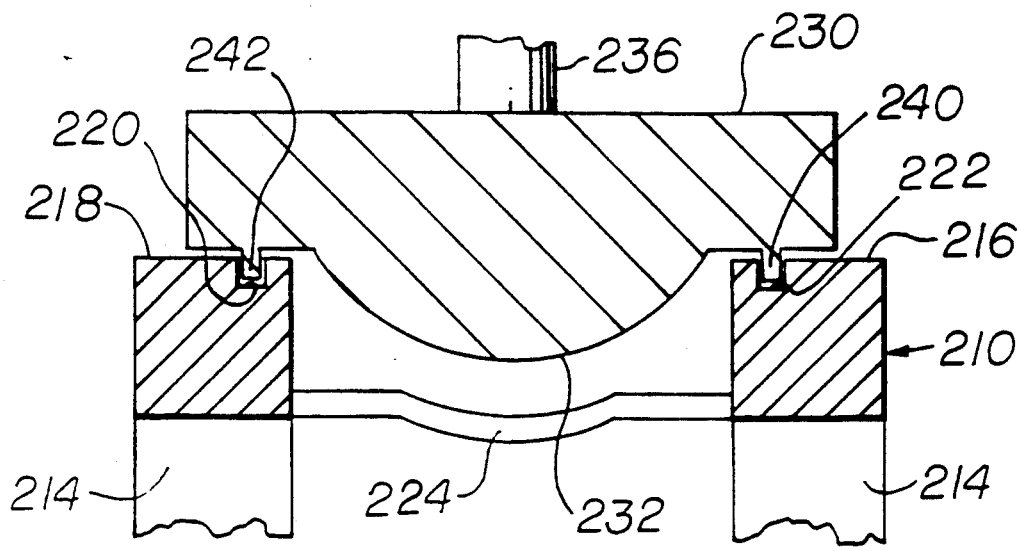
FIG. 7 is a cross-sectional view of a still further embodiment of the U-shaped bracket used with a cutting tool according to the invention, also taken along a cross-section similar to that of FIG. 3.

FIGS. 6 and 7 represent alternative embodiments of track configurations with appropriately modified track engaging surfaces on the cutting tool. Firstly, in FIG. 6 there is seen a modified cutting guide element 110 having anterior arms 114 and distal elements 116 and 118, the surfaces of which, adjoining the central opening therebetween, are provided with raised rail track members 120 and 122. As also seen in FIG. 6, the cutter 130 is provided with track engaging grooves 140 and 142 which are adapted to engage the raised rail track elements and guide cutter 130 in an appropriate path to form a resected patellar groove.

FIG. 7 shows in analogous fashion a revised embodiment in which channels 220 and 222 form the track means in the distal surfaces 216 and 218 of guide element 210. In this configuration, the track engaging portions 240 and 242 of cutting tool 230 comprised track engaging projections on the flanges provided on each side of the cutting surface 232. In other respects, the embodiments of FIG. 6 and 7 have other components analogous to those shown in FIGS. 1 through 5.

Figure 8:
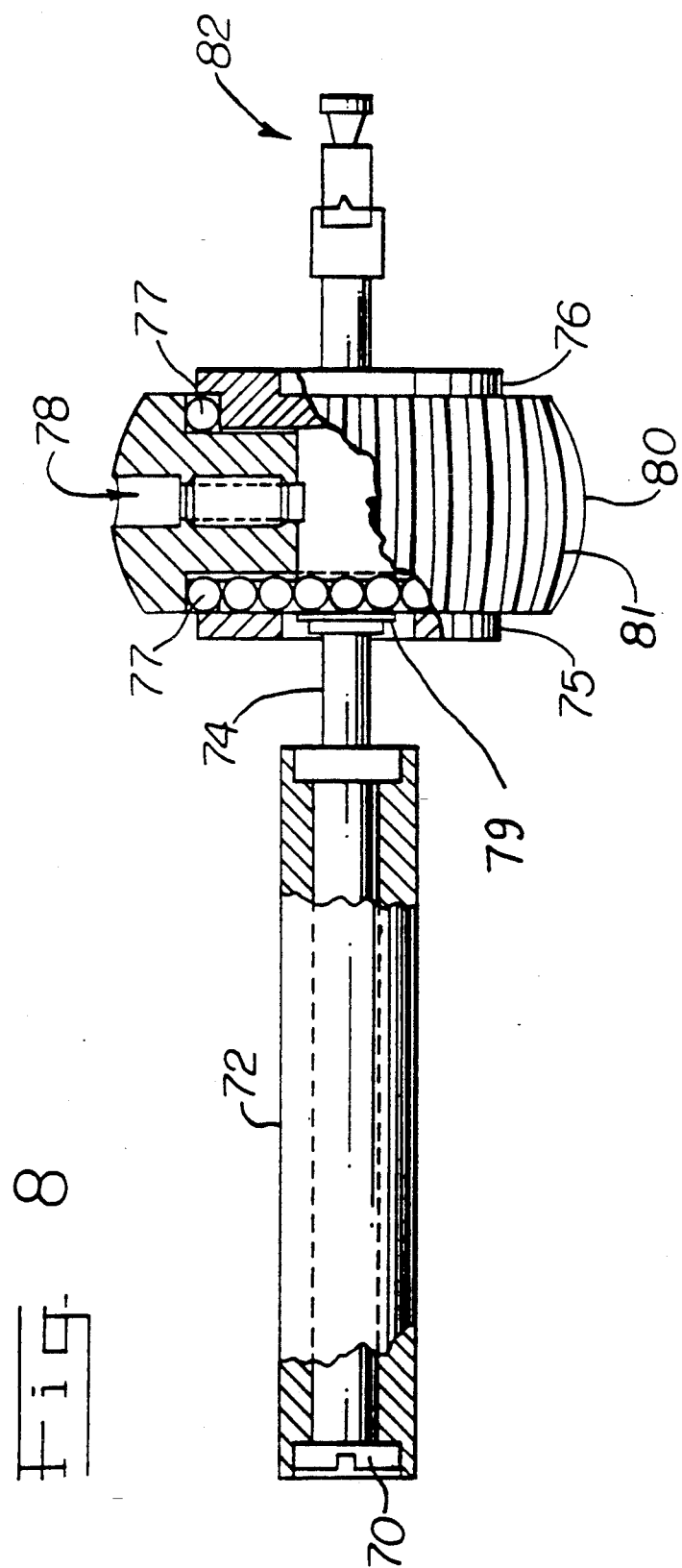
FIG. 8 is a side view of a further embodiment of a power driven rotary cutter for use in combination with the U-shaped bracket according to the invention, with parts shown in cross-section.

FIG. 8 shows a preferred embodiment of a rotary cutter for use in connection with the combination of the present invention. In that embodiment that cutting element is power driven while the track engaging surfaces are free to rotate separately therefrom. A handle 72 is rotatably affixed to one end of power driven shaft 74, for example, by a screw 70. Handle 72 may be formed from polytetrafluoroethylene or other low friction materials. A cutter 80 provided with cutting teeth 81 is affixed to shaft 74 by means of set screw 78. On each side of the cutting element 80 is an indentation or race 77 containing ball bearings which allow guide track engaging discs 75 and 76 to rotate separately from shaft 74. Appropriate mechanical connectors such as snap ring 79, which may fit into a groove on shaft 74, are utilized to hold the cutter in position on the shaft. The power drive end shaft 74 is provided with an appropriate connector to permit attachment to a rotary power driving device. For example, end 82 may be a "Hudson ®" end which attaches to a power reamer drive.

The ball bearings as shown in races 77 may be replaced, for example, by polytetrafluoroethylene washers or other low friction washers such as ultra high molecular weight polyethylene or nylon or the like.

It has been found that due to the fact that washers 75 and 76 are free wheeling from power shaft 74, the cutter 80 will not jump out of the track if the shaft is inadvertently twisted. Forcible pulling of the cutter along the track and excessive wear of the track is also obviated by this preferred embodiment.

In practicing the present invention, a surgeon would follow normal procedures for resection of the distal femur which would be resected to a size adapted to fit the dimensions of the particular guide unit 10 being employed. In general, the surgeon can observe a remaining part of the original patellar track between the resected condyles and can center the guide element 10 on such track. In the event that the track is not sufficiently observable after resection, the surgeon would center the guide 10 on the posterior condyles themselves. The guide element 10 would generally be provided to the surgeon in a number of separate sizes which would match the corresponding implant sizes provided to the surgeon. Resection of a groove by the cutting tool to the depth permitted by the guide will ensure a proper depth and placement of the newly formed patellar track.

Modular surgical instrumentation and a method of using same is further provided according to the invention, and shown in FIGS. 9 and 10. The instrumentation comprises the U-shaped bracket 10 (FIGS. 1-2) defining a generally U-shaped structure which is seated on the distal aspect of the resected femur 13 and the elongated central opening 23 appointed to expose a selected area of the femur, including curved ledges 40, 42 for guiding the tool 30 along a predetermined path for controlled shaping of a curved patellar groove in a portion of the selected area exposed through the opening. A second bracket generally indicated at 300 defines a linear bore 302 which guides an end mill, generally indicated at 304 rotating in the direction of arrow 306, in an axial direction shown by arrow 308 downwardly toward the resected femur 13, i.e., essentially parallel to the long axis of the intermedullary femoral (not shown). The bore 302 has a pair of slots 310 which extend tangentially from the bore 302 for guiding a U-shaped punch 312 downwardly (arrow 308) through the bore 302 to form, together with the end mill 304, a relatively deep recess accommodating an intercondylar stabilizing housing of a knee implant (not shown) a bracket 300 further comprises a top plate 314 which is essentially perpendicular to the long axis of the femur and through which the bore 302 is formed.

Extending perpendicularly from the top plate 314 are a pair of legs 316 each having seats 318 which extend in an anterior-posterior direction and have a curved shape to engage the ledges 40, 42 of the U-shaped bracket 10. The top plate 314 of the bracket 300 has an extended arm 320 which is aligned with respect to the U-shaped bracket 10 by means of a positioning slot 322 which engages a peg 324 projecting distally from the bracket 10. A tightening screw 326 projects inward a medial-lateral direction through the arm 320 and engages the bracket 10 to securely lock the bracket 300 into proper position with respect to the U-shaped bracket 10.

The end mill 304, shown in FIG. 9, has a shoulder 328 which bottoms-out in the stop 330 formed at the distal end of the bore 302. After the end mill 304 is brought down into the surface of the resected femur 13 and withdrawn, the punch 312 is impacted with a mallet or the like to finish forming the deep recess for the intercondylar stabilizing housing, until the tip 332 of the punch 312 reaches the bottom of the hole formed by the end mill 304.

The method of the invention comprises the steps of seating the first bracket described above on the distal aspect of the resected femur and moving the first shaping tool along the curved track to form a patellar groove in a selected area thereof. The first shaping tool is then withdrawn and, leaving the first bracket in place, the second bracket described above is seated on the curved track so that the slotted bore of the second bracket is accurately aligned with the opening of the first bracket, after which a second shaping tool is introduced through the bore to form a recess accommodating the intercondylar-stabilizing housing of the implant. Preferably, the first shaping tool comprises end mill 304 and the second shaping tool comprises punch 312 which, according to the method of the invention, together form the recess (not shown) accommodating the intercondylar stabilizing housing of the implant.

While a number of embodiments of the invention have been disclosed herein, further revisions and alternative embodiments falling within the scope and spirit of the appendant claims will be apparent to those skilled in the art.

What is claimed is:

1. Surgical instrumentation comprising, in combination:
    (a) a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove in a first trochlear portion of the selected area exposed through the opening;
    (b) a second bracket including a base presenting a proximally-facing contact surface and means for supporting the base in releasable engagement with the track, including a bore extending through the base in a longitudinal direction generally parallel to the long axis of the femur for guiding a second shaping tool in forming a relatively deep recess in a second portion of the selected area exposed through the opening for accommodating an intercondylar stabilized housing of a knee implant in the femur; and
    (c) means for accurately aligning the bore relative to the opening whole forming the recess.

2. The instrumentation of claim 1 wherein the bore further comprises a cylindrical aperture having a pair of tangentially-formed slots extending along the length of the aperture.

3. The instrumentation of claim 2 wherein the second shaping tool further comprises an end mill.

4. The instrumentation of claim 3 wherein the bore has a stop and the end mill has a shoulder which bottoms-out in the stop, controlling the depth of the recess being thereby formed.

5. The instrumentation of claim 3 further comprising a punch having a generally U-shaped cross-section which corresponds to that of the slotted bore and is received therein to cut away the remaining bone for the housing recess.

6. The instrumentation of claim 5 wherein the punch further comprises a sharpened U-shaped edge which bottoms-out a common proximal distance into the femur with the end mill.

7. The instrumentation of claim 1 wherein the track further comprises a pair of ledges extending along the edges of the elongated opening of the first bracket, the support means including a pair of legs extending from the base of the second bracket on opposed sides of the opening and terminating in a pair of proximally-facing contoured seats which engage the ledges.

8. The instrumentation of claim 1 wherein the alignment means further comprises an attachment peg extending distally from the first bracket and engaging a cooperating slot formed in the second bracket which is oriented in a lateral-medial direction.

9. A method of implanting a condylar prosthesis of the type having an intercondylar stabilizing housing, the method comprising the steps of:
    (a) providing the instrumentation of claim 1, seating the first bracket thereof on the distal aspect of a resected femur and moving the first shaping tool along the curved track to form a patellar groove in a selected area thereof;
    (b) withdrawing the first shaping tool, leaving the first bracket seated on the femur;
    (c) seating the second bracket securely on the curved track so that the bore of the second bracket is accurately aligned with the opening of the first bracket; and
    (d) moving a second shaping tool through the bore to form a recess accommodating the intercondylar-stabilizing housing of the implant.

10. The method of claim 9 further comprising the steps of: providing an end mill as the second shaping tool and moving the end mill through the bore to form a hole in the femur; providing a pair of tangential slots in the bore which extend the length thereof; providing a punch with a generally U-shaped cross-section and moving the punch through the slotted bore to contact the bottom of the hole and form the recess to accommodate the housing of the implant.

11. Surgical instrumentation comprising, in combination:
  (a) a first bracket defining a generallly U-shaped structure having an internal surface adapted to be seated on the distal aspect of a resected femur and an elongated central opening appointed to expose a selected area of the resected femur, including a curved track for guiding a first shaping tool along a predetermined path for controlled shaping of a curved patellar groove in a trochlear portion of the selected area exposed through the opening;
  (b) a second bracket including a base presenting a proximally-facing contact surface and means for supporting the base in releasable engagement with the track, including a bore extending through the base with a generally cylindrical aperture and a pair of tangentially-formed slots extending the length of the aperture, the aperture having an axis generally parallel to the long axis of the femur and a stop located at a selected depth with the aperture;
  (c) an end mill which is received within and guided by the aperture for forming a relatively deep recess in the femur to accommodate an intercondylar stabilizing housing of a knee implant, including a shoulder which bottoms-out in the stop, controlling the depth of the recess being thereby formed;
  (d) a punch having a generally U-shaped cross-section corresponding to that of the slotted aperture and being received therein to cut away the remaining bore for the housing recess, including a sharpened U-shaped edge which bottoms-out a common proximal distance into the femur with the end mill; and
  (e) means for accurately aligning the bore relative to the opening while forming the recess.

* * * * *